(12) United States Patent
Hoch et al.

(10) Patent No.: US 9,101,374 B1
(45) Date of Patent: Aug. 11, 2015

(54) METHOD FOR GUIDING AN ABLATION CATHETER BASED ON REAL TIME INTRACARDIAC ELECTRICAL SIGNALS AND APPARATUS FOR PERFORMING THE METHOD

(71) Applicants: David Harris Hoch, Brookville, NY (US); Ethan Gregory Hoch, Brookville, NY (US); Stuart Owen Schecter, Great Neck, NY (US)

(72) Inventors: David Harris Hoch, Brookville, NY (US); Ethan Gregory Hoch, Brookville, NY (US); Stuart Owen Schecter, Great Neck, NY (US)

( * ) Notice: Subject to any disclaimer, the term of this patent is extended or adjusted under 35 U.S.C. 154(b) by 129 days.

(21) Appl. No.: 13/960,880

(22) Filed: Aug. 7, 2013

Related U.S. Application Data

(60) Provisional application No. 61/742,296, filed on Aug. 7, 2012.

(51) Int. Cl.
*A61B 18/12* (2006.01)
*A61B 18/18* (2006.01)
*A61B 18/00* (2006.01)

(52) U.S. Cl.
CPC ............... *A61B 18/18* (2013.01); *A61B 18/12* (2013.01); *A61B 2018/00351* (2013.01); *A61B 2018/00773* (2013.01)

(58) Field of Classification Search
CPC ............ A61B 2018/00351; A61B 2018/00636; A61B 2018/00904; A61B 8/4254
USPC ....................................................... 606/34, 41
See application file for complete search history.

(56) References Cited

U.S. PATENT DOCUMENTS

| 4,844,062 | A | 7/1989 | Wells |
| 5,429,604 | A | 7/1995 | Hammersmark |
| 5,484,433 | A | 1/1996 | Taylor |
| 5,571,088 | A | 11/1996 | Lennox |
| 5,836,946 | A | 11/1998 | Diaz |
| 2004/0059237 | A1* | 3/2004 | Narayan et al. ............... 600/509 |
| 2008/0200913 | A1* | 8/2008 | Viswanathan .................. 606/41 |
| 2013/0116681 | A1* | 5/2013 | Zhang ............................. 606/34 |
| 2013/0211399 | A1* | 8/2013 | Caples et al. .................. 606/41 |

* cited by examiner

*Primary Examiner* — Ronald Hupczey
*Assistant Examiner* — Bo Ouyang
(74) *Attorney, Agent, or Firm* — Gottlieb, Rackman & Reisman, PC

(57) ABSTRACT

An apparatus and method for controlling the orientation, geometry, shape or length of an inserted catheter is provided to optimize it's position during procedures for treating cardiac arrhythmia by ablation based on functions derived from one or more parameters including the temporal relationship between intracardiac signals, patient anatomy, cardiac tissue electrical properties, imaging data, and other criteria that may include previously stored data collected from one or more patients who have had successful therapy delivered.

4 Claims, 4 Drawing Sheets

METHOD FOR GUIDING AN ABLATION CATHETER BASED ON REAL TIME INTRACARDIAC ELECTRICAL SIGNALS AND APPARATUS FOR PERFORMING THE METHOD

RELATED APPLICATIONS

This application claims priority to U.S. Provisional Application Ser. No. 61/742,296 filed Aug. 7, 2012, and incorporated herein by reference in its entirety.

BACKGROUND OF THE INVENTION

A. Field of Invention

The present application pertains to a method and apparatus for guiding an ablation catheter automatically using cardiac signals sensed in real time.

B. Description of the Prior Art

Catheter ablation is a surgical technique used for treating patients with cardiac arrhythmia (such as supraventricular tachycardia or SVT) or other illnesses when the patient does not respond to medicine. The procedure involves interrupting or otherwise altering electrical pathways in the heart by applying energy to specific pathological cardiac tissues.

Currently available cardiac catheters are used to apply thermal, RF, or cryogenic energy to perform ablation. Typically, these catheters are fairly complex and include guiding elements for guiding the distal aspect or end of the catheter, sensor electrodes for sensing intrinsic electrical pathways or conductive tissue in the heart, as well as active electrodes that provide the actual energy for the procedure once the desired cardiac tissue is reached.

The distal end of the catheter can be manipulated and modified by an operator using manual controls to position it in contact with diseased cardiac tissue for delivery of ablative energy for cauterizing abnormal conductive tissue. Catheters of a variety of catheter shapes and sizes are available from numerous manufacturers (such as Boston Scientific, Medtronic, and Biosense Webster) and many catheters are designed to be deformable using mechanisms incorporated onto a hand held controller with triggers, knobs or collars as are understood in the art.

However, such catheters are limited in their ability to detect and localize electrical pathways that are aberrant and often require prolonged attempts by the operator for proper positioning thereof for the procedure to be successful. This prolonged process increases the risk of complications and duration of radiation exposure.

Medical catheters and sheaths are generally tubular shaped and of a sufficiently small diameter to be inserted into a patient's body through a small incision, puncture or a natural opening. Such catheters can include mechanisms to deploy inner catheters, cardiac leads, electrodes, deliver contrast (e.g. radiopaque dye) or ablative energy (e.g. current, radiofrequency energy, light, ultrasound), and are often flexible.

By way of example, a catheter capable of delivering electrical energy has been developed by Diaz et. al. (U.S. Pat. No. 5,836,946). This catheter allows for transmitted electrical energy along an outer layer of stranded conductive fibers that delivers electrical energy through a cutting tip for multipolar electro-cautery. Wells (U.S. Pat. No. 4,844,062) describes a rotating fiber optic laser catheter assembly with an eccentric lumen that provides for the ablation of obstruction in vessels such as coronary arteries via transmitted laser energy. Taylor et al (U.S. Pat. No. 5,484,433) patented a deflectable tissue-ablating device that uses a plurality of optical fibers for delivery of light energy. Hammersmark et al. (U.S. Pat. No. 5,429,604) developed a fiber optic catheter with a twistable tip. Such technology is implemented for accessing various anatomic locations such as about the pulmonary veins, atria-ventricular node, and accessory pathways. Cardiac and vascular perforations are complications associated with these procedures.

Mechanisms for deflecting catheters are well known in the art (e.g. Lennox, et al. U.S. Pat. No. 5,571,088). More particularly, designs for controlled deflection of the distal aspect of the catheter shaft are known using a pull-wire that extends from a handle at the proximal end of the catheter through a lumen in catheter shaft and is fastened to distal end of the catheter shaft. Such a design is constructed such that the distal end is more flexible then the proximal segment. In this fashion, when the handle is pulled back the pull wire causes distal end to bend preferentially from an un-deflected position to a deflected position. The distal tip of the catheter shaft can be brought into contact with a wall of heart by controllably deflecting the distal end of the catheter. The electrode senses electrical potentials within the heart for the purpose of locating cardiac tissue containing abnormal electrical pathways and the operator can apply radiofrequency current to the electrode at distal tip for ablation of localized cardiac tissue. This mechanism does not ensure tissue contact nor does it serve to anatomically locate the treating portion of the distal member into the proper location for delivery of therapy.

Thus, there is a need for a method to optimize the location of the catheter's distal end where therapy is delivered to pathologic tissue, and an apparatus for performing the method.

SUMMARY OF THE INVENTION

Supraventricular tachycardia is a common cardiac arrhythmia with a prevalence of 3 out of 1000 people. Atrioventricular nodal reentry (AVNRT) is the most common accounting for more than 50% of such cases. AVNRT involves a fast anterior and a slow posterior pathway. Ablation to the slow pathway is the standard curative procedure. Prior techniques for ablation to the slow pathway have involved anatomic features and electrical signals but not in an efficient tailored approach. Over the last 25 years one of the present inventors has performed approximately 3000 ablations for AVNRT and developed a stepwise approach with high cure rates (98%) and minimal complications (<1/1000 pacemaker risk)—at least ten times better than reported literature. The approach involves initially positioning the ablation catheter in the standard HIS Bundle position with equal atrial and ventricular electrograms and a significant HIS Bundle recording. The tip of the catheter is than moved inferiorly and posteriorly with loss of the HIS Bundle recording and adjusted to a 4:1 ratio of ventricular to atrial recording. This electro-anatomic approach can be automated with processing of electrical signals to direct the movement of the catheter.

The current invention provides for a catheter that acquires intracardiac electrical signals and analyzes the temporal relationship and other characteristics of these signals at different anatomic locations. This is done in order to optimize the shape (e.g., deflection, curvature) and length of the catheter for ablation or reentrant supraventricular tachycardia. These temporal relationships have been noted by the inventors to correlate with both the anatomic location of aberrant electrical pathways and the most desirable shape/geometry of the catheter's distal aspect.

DETAILED DESCRIPTION

Figure 3:
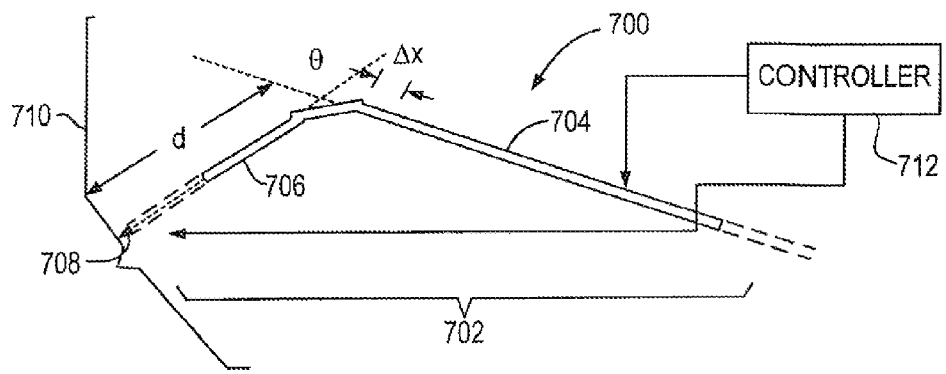
FIG. 3 shows the distal aspect or end of an ablation catheter.

As shown in FIG. 3, a typical ablation catheter 700 includes an elongate body with a distal aspect or end 702. The catheter body is composed of flexible material such as a thermoplastic polymer or similar material/composite with a central lumen (not shown). The catheter 700 includes several electrodes for mapping electrical activity in the heart as is commonly understood by those experienced in the art. The central lumen can house inner wires, catheters, deliver therapeutic agents or aspirate fluid such as blood.

Unfortunately, as conventionally designed catheters pass through a patient's tissues and vasculature the operator looses his or her ability to manipulate the catheter's exact location and position it proximate to the cardiac tissue being evaluated or treated due to the operator's forces at the insertion site, attenuation or frictional effects form bodily tissues and the compliant nature of the inserted catheters.

The current invention acquires intracardiac signals, defines the temporal relationship between the signals from different anatomic sites and determines the location where aberrant, pathologic tissue should be ablated. Intracardiac signals can be acquired by methods understood by those experienced in the art, such as bipolar, unipolar and/or multipolar electrodes. Based on this data, the catheter automatically curves, deflects, extends and/or retracts so as to position the distal aspect of the catheter where therapeutic energy is delivered in contact with the diseased tissue based on a function as described in more detail below. The catheter's length, position and curvature are controlled by mechanisms known in the art and include but are not limited to pulley systems, retractable wiring, deflectable cables, screw and unscrew-based mechanisms. Other methods for telescoping and retracting the terminal ablation treatment member of the catheter can be implemented, and the like and are in no way limited in scope or spirit. By way of example, these methods may include pneumatic, hydraulic, magnetic, electromagnetic systems. More specifically, referring to FIG. 3, the distal aspect of the catheter 700 includes a section 704 that is an extension of the main body and section 706 terminating in an electrode 708. The electrode 708 is used to perform the ablation when the electrode is in contact with the targeted tissue 710. The position of electrode 708 can be fine tuned by changing angle θ between sections 704, 708, and/or the length of section d using automated catheter controller 712.

Figure 4:
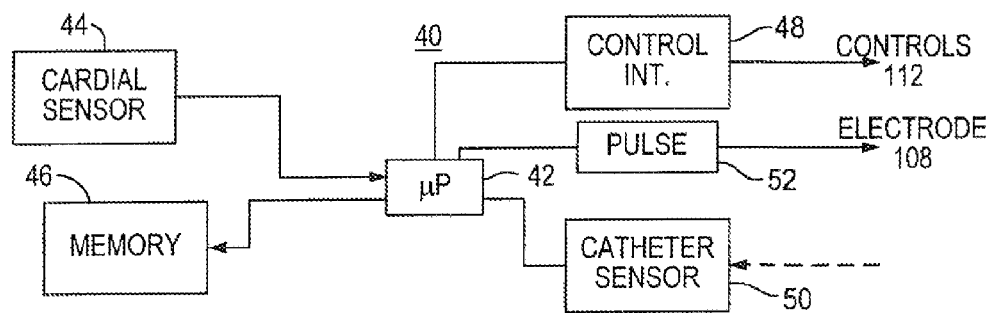
FIG. 4 shows a block diagram of the subject apparatus.

FIG. 4 shows a block diagram of an apparatus 40 constructed in accordance with this invention. The apparatus 40 includes a microprocessor 42. The microprocessor 42 receives signals indicative of cardiac activity through sensors 44. The sensed signals and various other data are stored in memory 46. A control interface 48 receives command signals from the microprocessor for changing the position of the distal aspect 702 of catheter 700. In response to these command signals, the interface provides appropriate commands to the catheter controller 712. The position of the distal aspect 702 is monitored through a catheter monitor 50. Once the microprocessor 42 determines that the distal aspect is in the proper position, a pulse generator 52 is activated to send ablation signals to electrode 108.

In a preferred embodiment of the invention for the ablation of cardiac tissue in patients suffering from atria-ventricular (AV) nodal re-entry, is descriptive, but in no way is the current invention limited to treatment of any specific pathologic state, in scope or spirit. By way of example, an equation or function can be derived based on data compiled from a series of patients undergoing ablation of a re-entrant circuit that causes AV re-entry, or other re-entrant rhythm such as Wolf Parkinson White syndrome and derived based on alternate methodologies as described below. Methods for identifying the ideal position for ablation of pathologic tissue includes but is not limited to radiographic, magnetic, electromagnetic, ultrasonic, impedance, electrical, resistive, or any navigational system commonly used during electrophysiologic procedures.

Figure 1:
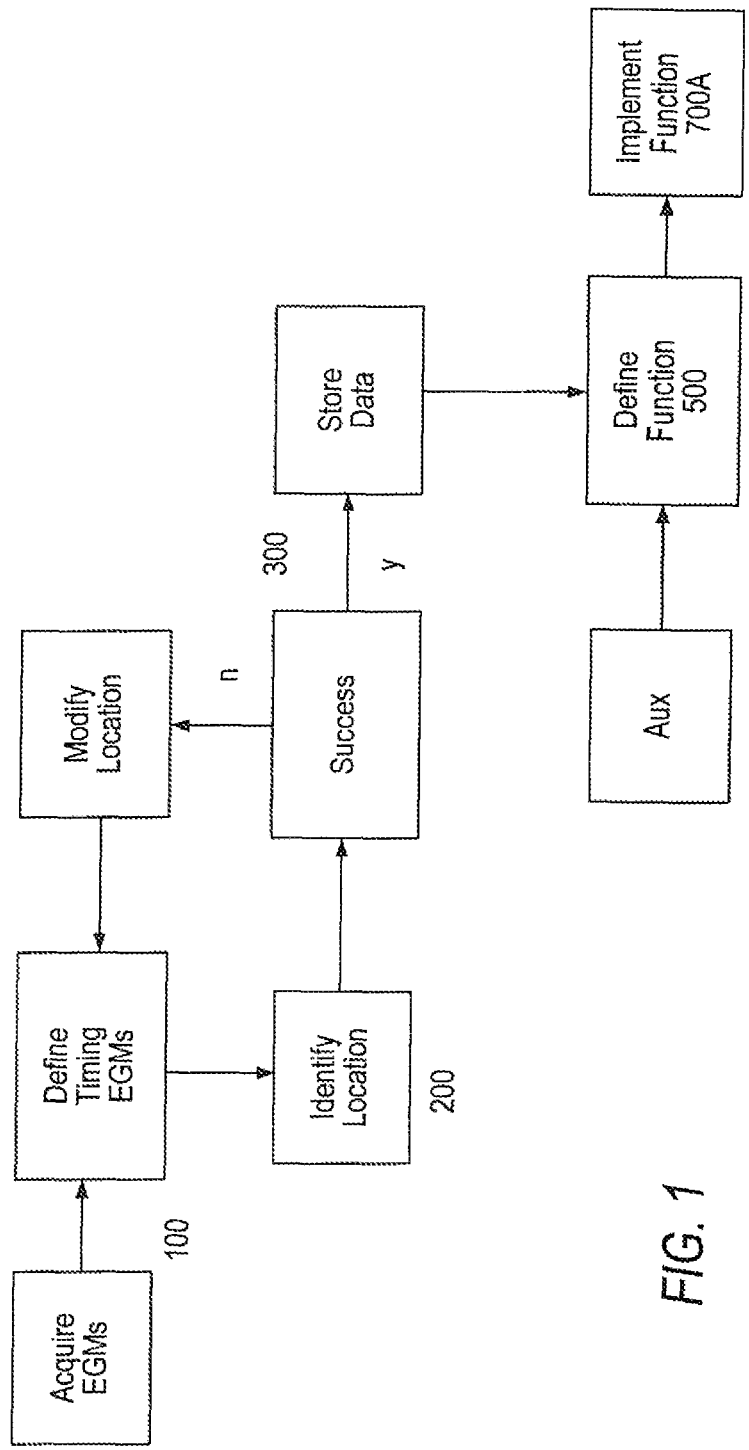
FIG. 1 shows a somewhat diagrammatic flow chart illustrating how information is acquired by the apparatus of the present invention.

In a preferred embodiment, the apparatus can be optimized as more patients undergo ablation and one or more functions are derived based on utilization and success during successive procedures. Referring to FIG. 1, the timing of acquired cardiac electrical signals, or EGMs is defined and stored at step 100 in memory. The location of the catheters distal aspect and geometric properties (length, curvatures etc.) are noted and stored at step 200. If treatment is successful (e.g. aberrant conductive pathway ablated) then the data is stored (e.g., in a look up table) at step 300 as being suitable for the electrogram signals acquired. Suitability or treatment success can be defined manually by the operator inputting signal from a controller, that recurrent arrhythmia is not present or even automatically if not, the catheter's position is modified. This modification can be done manually by the operator and/or automatically or semi-automatically based on prior data from previous procedures and/or auxiliary input data, or be programmed based on equations, of which examples are provided herein. The entire process can be done manually or robotically, semi-automatically or automatically. After the needed data is collected or generated, a relationship or function is determined that correlates the appropriate orientation, shape and geometry of the catheter for each patient. Additional data including data related to the patient's anatomy, physiological properties and the like can also be accounted for and incorporated into the function (aux in FIG. 1) and used to optimize system functionality as additional patients have similar procedures performed with the system.

By way of example, a function (herein referred to as the positioning function) is derived based on the aggregate of a number of cases being performed with the system. The function can be a logarithmic equation:

$$\Delta x = (4.7059 * \ln(A/V) + 5.1429)/\cos(\theta) \, (mm)$$

Where θ is defined in FIG. 3, A/V is the ratio of the sensed atrial and ventricular signals and Δx is the desired change of position of the electrode 108. Other functions including but not limited to linear, non-linear, and exponential relationships can be used to define the catheter's geometry/properties. Alternatively or additionally, electrical information related to activation sequence of aberrant cardiac conductive pathways at the tissue catheter interface could be accounted for when determining catheter position, shape, and geometry. Such electrical information can be acquired using sensors known by those experienced in the art and include but are in no way limited to contact and non-contact sensors. Changes in the shape/geometry of the inserted catheter can be at one or more locations and one or more algorithms can be implemented to control the shape and geometry of the catheter at one or more locations. Neural networks can also be used for system optimization.

Figure 2:
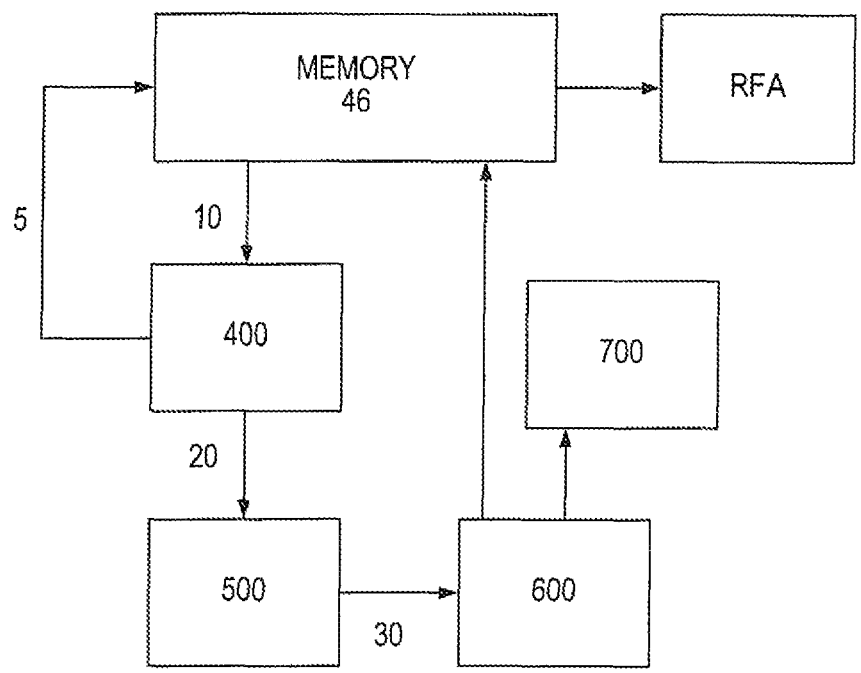
FIG. 2 shows a somewhat diagrammatic flow chart illustrating the operation of the subject apparatus.

Referring to FIG. 2, an exemplary simplified process is depicted for optimizing catheter shape, deformation, curvature, using modules preferably implemented as software. The operator positions the catheter (FIG. 3) at an estimated location for delivering radiofrequency energy (RFA). Intracardiac electrograms characteristics obtained from two or more electrodes are acquired, analyzed, and stored in memory 46. This composite data consists of temporal information (e.g. interval timing, cycle length of arrhythmia, conduction times between electrodes), spatial information (e.g., anatomic/geometric location as defined by externally located navigational systems, radiographic or magnetic data), signal amplitude (e.g., peak positive deflection, peak negative deflection, rectified signal amplitude, etc.), impedance values characteristic of adequate tissue contact, temperature, or other relevant indices.

At step 10, the composite data is input into as digital acquisition data (DAQ) in a first analyzer module 400 and analyzed to confirm adequate signal quality (e.g., signal to noise ratio) prior to being input (step 20) into a second analyzer module 500. If the data is inadequate, repeat data acquisition occurs (step 5). In module 500, the relevant data/numerical values are entered into the previously derived positioning function (defined by way of example in FIG. 1). Module 500 then outputs commands at step 30 to controller 600 which modifies the position of the catheter's distal end by adjusting the curvature, extension, retraction, deformation, etc. of the catheter proper using methods that include but are not limited to those as known by those experienced in the art. These methods can include a pulley system modifying the distal aspect of the inserted catheter as to make the angle more or less acute, an extension mechanism that screws or unscrews a telescoping portion of the distal aspect of the catheter clockwise or counterclockwise resulting in a lengthening or shortening (dashed arrow) of the terminal distance, d, of the catheter as depicted in FIG. 3. These methods can include mechanisms as known by those experienced in the art and described in the references disclosed.

In one preferred embodiment, the data is stored and images of the catheter position/location/shape are registered in a visual display by a display module 700A. Repeat data acquisition stored in memory is applied upon confirmation of adequate catheter location and tissue contact as well as other relevant properties (e.g., temperature, impedance). Relevant properties include but are not limited to indices that may be indicative of tissue injury, risk of complications (e.g., heart block), etc.

In an alternate embodiment of the invention, the duration of RFA is determined based on DAQ as to ensure safe and efficacious elimination of cardiac arrhythmia. These modules are implemented by the apparatus of FIG. 4.

Figure 5:
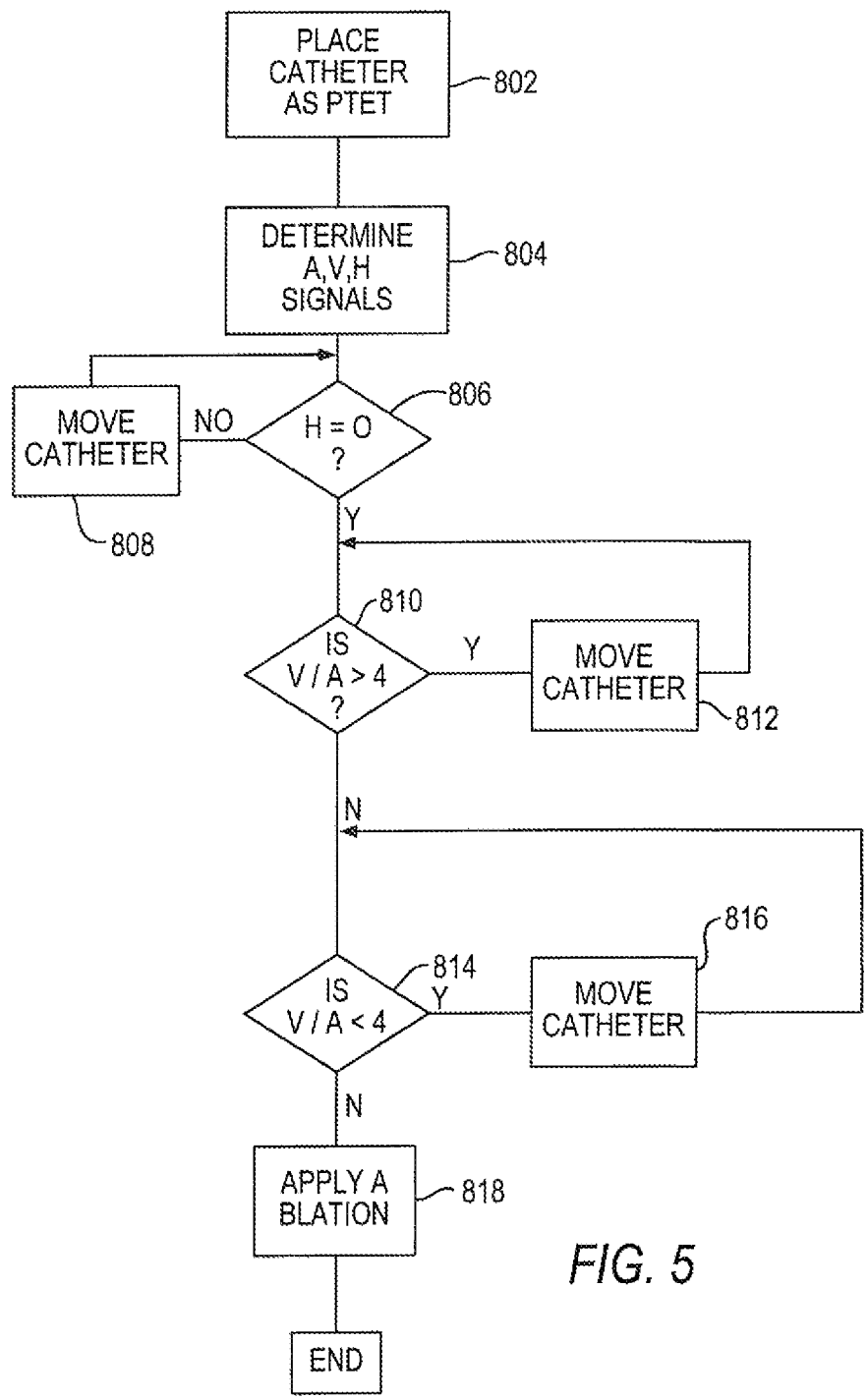
FIG. 5 shows a detailed flow chart for one embodiment of the subject method.

In one specific embodiment of the invention, an ablation procedure is performed as follows. First, a catheter is inserted into the patient and positioned using conventional means (step 802 FIG. 5). Next, cardiac activity is sensed and signals from the atrial, ventricle and the His node are acquired (signals A, V, H) (step 804). In step 806 a test is performed to determine if there are any sensed signals from the His node. If there are, the catheter is moved (step 808) and the test is repeated until no His signal is sensed. Next, in step 810 a predetermined parameter is checked to see if it is above a predetermined threshold. As discussed above, various parameters may be used for this determination. In one embodiment, the ratio V/A (the ventrical sensed signal/atrial sensed signal) is used as the parameter. If this parameter is larger than 4.0 then the catheter is moved (step 812). Preferably for this parameter, the catheter is moved proximally. The test of step 810 is then repeated.

In step 814 a test is performed to determine if the parameter (e.g. A/V) is <4.0 if it is then the catheter is moved (step 816) preferably distally.

In both steps 810 and 814 the threshold is indicated as being 4.0. Obviously a range is used for these tests, such as ±10-25%. Moreover, while the tests 810, 814 are discussed separately, they can be performed simultaneously as well.

Finally, in step 818 ablation applied through the electrode 708.

Numerous modifications may be made to the invention without departing from its scope as defined in the appended claims.

We claim:

1. A method of automatically performing ablation on a cardiac tissue using a catheter adapted to be inserted into the heart and having an electrode and an apparatus coupled to said catheter, said method comprising the steps of:
    inserting a catheter into the heart;
    sensing electrical cardiac activity with said apparatus to determine if the electrode is in contact with a tissue requiring ablation by sensing activity from the His node;
    determining automatically if activity from the His node meets a first criteria with said apparatus;
    moving the electrode automatically if the first criteria is not met;
    repeating the determining and moving steps until said first criteria is met;
    sensing activity from the atrium and the ventricle after the first criteria has been met and moving said catheter until activities from the atrium and ventricle meet a second criteria; and
    applying an ablation signal through said electrode.

2. The method of claim 1 wherein said ablation signal is selected to prevent reentrant supraventricular arrhythmia.

3. The method of claim 1 wherein said determining includes comparing a cardiac parameter dependent on said sensing to a threshold.

4. The method of claim 1 wherein said activity is expressed as a ratio of a parameter from the ventricle to a parameter from the atrium.

* * * * *